US009486346B2

(12) United States Patent
Argentine (10) Patent No.: US 9,486,346 B2
(45) Date of Patent: Nov. 8, 2016

(54) BALLOON EXPANDABLE STENT GRAFT AND APPARATUS AND METHOD FOR EXPANDING A BALLOON EXPANDABLE STENT GRAFT

(71) Applicant: Medtronic Vascular, Inc., Santa Rosa, CA (US)

(72) Inventor: Jeffery Argentine, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 516 days.

(21) Appl. No.: 13/782,627

(22) Filed: Mar. 1, 2013

(65) Prior Publication Data

US 2014/0249617 A1 Sep. 4, 2014

(51) Int. Cl.
| | | |
|---|---|---|
| A61F 2/06 | (2013.01) | |
| A61F 2/958 | (2013.01) | |
| A61F 2/07 | (2013.01) | |
| A61F 2/82 | (2013.01) | |

(52) U.S. Cl.
CPC ............... *A61F 2/958* (2013.01); *A61F 2/07* (2013.01); *A61F 2002/828* (2013.01)

(58) Field of Classification Search
CPC ................................ A61F 2/958; A61F 2/97
See application file for complete search history.

(56) References Cited

U.S. PATENT DOCUMENTS

| | | | |
|---|---|---|---|
| 5,324,261 A | 6/1994 | Amundson et al. | |
| 5,370,614 A | 12/1994 | Amundson et al. | |
| 5,667,523 A * | 9/1997 | Bynon et al. | 623/1.13 |
| 6,004,348 A * | 12/1999 | Banas et al. | 623/23.7 |
| 6,120,477 A * | 9/2000 | Campbell | A61F 2/958 |
| | | | 604/96.01 |
| 6,451,050 B1 | 9/2002 | Rudakov et al. | |
| 2009/0069878 A1 | 3/2009 | Weber et al. | |
| 2013/0018406 A1* | 1/2013 | Campbell et al. | 606/194 |

FOREIGN PATENT DOCUMENTS

| | | |
|---|---|---|
| WO | WO97/07756 | 3/1997 |
| WO | WO97/40877 | 11/1997 |

OTHER PUBLICATIONS

PCT/US2014/016585, PCT International Search Report and Written Opinion, mailed Jul. 7, 2014.

* cited by examiner

*Primary Examiner* — Gregory Anderson (57) ABSTRACT

A stent-graft delivery system includes a balloon, a sleeve disposed over the balloon, and a stent graft mounted over the sleeve. The sleeve includes a weakened area between a first end and a second end of the sleeve such that when the balloon is expanded, the balloon expands from a center portion of the balloon towards the ends of the balloon. The weakened area of the sleeve may be a slit, a thinner wall section, grooves, notches, or other weakening features. The sleeve may be adhesively attached to an outer shaft of the catheter or to an outer surface of the balloon.

14 Claims, 9 Drawing Sheets

BALLOON EXPANDABLE STENT GRAFT AND APPARATUS AND METHOD FOR EXPANDING A BALLOON EXPANDABLE STENT GRAFT

FIELD OF THE INVENTION

The present invention relates generally to a balloon expandable stent and an apparatus and method for expanding a balloon expandable stent to reduce foreshortening in such a balloon expandable stent graft.

BACKGROUND OF THE INVENTION

Tubular prostheses, such as stents, grafts, and stent-grafts are known for treating abnormalities in various passageways of the human body. In vascular applications, these devices often are used to replace or bypass occluded, diseased or damaged blood vessels such as stenotic or aneurysmal vessels. For example, it is well known to use stent-grafts of a biocompatible graft material supported by a framework, for e.g., one or more stent or stent-like structures, to treat or isolate aneurysms. The framework provides mechanical support and the graft material or liner provides a blood barrier. When implanting a stent-graft, the stent-graft typically is placed so that one end of the stent-graft is situated proximal to or upstream of the diseased portion of the vessel and the other end of the stent-graft is situated distal to or downstream of the diseased portion of the vessel. In this manner, the stent-graft extends through and spans the aneurysmal sac and extends beyond the proximal and distal ends thereof to replace or bypass the dilated wall.

Such tubular prostheses are known to be implanted in either an open surgical procedure or by a minimally invasive endovascular/endoluminal approach. Minimally invasive endovascular stent-grafts for use in treating aneurysms are often preferred over traditional open surgery techniques where the diseased vessel is surgically opened, and a graft is sutured into position bypassing the aneurysm. The endovascular approach generally involves opening a vein or artery with a needle, inserting a guidewire into the vein or artery through the lumen of the needle, withdrawing the needle, inserting over the guidewire a dilator located inside an associated sheath introducer having a hemostasis valve, removing the dilator and inserting a delivery catheter through the hemostasis valve and sheath introducer into the blood vessel. The delivery catheter with the stent-graft secured therein may then be routed through the vasculature to the target site. For example, a stent-graft delivery catheter loaded with a stent-graft can be percutaneously introduced into the vasculature, for e.g., into a femoral artery, and the stent-graft delivered endovascularly across an aneurysm where it is then deployed.

Specialized endovascular stent-grafts have been developed for the treatment of thoracic aortic aneurysms. A thoracic aortic aneurysm a bulge that forms in the wall of the aorta in the area of the aortic arch or just below the aortic arch. Emanating from the aortic arch are three branch arteries, the innominate or brachiocephalic artery, the left common carotid artery, and the left subclavian artery. In some cases, an aneurysm in the aortic arch may extend into one of the branch arteries, or the aneurysm is located in the arch such that a main stent graft used to bypass the aneurysm will block access to the one or more of the branch arteries. Accordingly, a branch stent graft may extend through a fenestration in the main stent graft and extend into the branch artery.

However, the aortic arch represents a challenging design environment due to a significant amount of cardiac and reparatory movement. Such movement requires a branch stent graft with significant flexibility and durability to withstand such movement over and extended period of time. Further, in some cases, the fenestration of the main stent graft is not aligned with the branch artery. In such cases, the branch stent graft extends from the fenestration in the main stent graft, extends within the aorta for a short distance, and then extends into the branch artery (offset configuration). In such situations, significant flexibility is required and sufficient radial force to maintain the branch stent graft open against the force of the main stent graft while in the aorta.

Currently there are no commercially available branch stent grafts specifically designed for the aortic arch. Branch stent grafts used for other areas are not suitable for use in the aortic arch branch arteries. Known self expanding stent grafts lack the radial force required to perfuse the side branch, especially if the fenestrated aortic stent graft is deployed in an offset configuration. Known balloon expandable stent grafts are generally too stiff to decouple the large amount of motion occurring in the arch from the perfused branch vessel and these rigid stents may fracture. Accordingly, there is a need for a branch stent graft with sufficient flexibility and durability to withstand forces in the aortic arch.

With some balloon expandable stents or stent grafts, there can be a problem with foreshortening of the stent or stent graft when it is expanded by the balloon. Foreshortening results in a stent or stent graft that, when expanded to its radially expanded configuration, is shorter than expected or desired. In such a situation, the stent or stent graft does not cover the desired length of a treatment site, resulting in an untreated area or requiring delivery of an additional stent or stent graft to cover the untreated area. Foreshortening may occur due to the design of the stent and the fact that the balloon is generally slightly longer than the stent or stent graft disposed thereon. Because the stent or stent graft resists expansion of the balloon where the stent or stent graft is mounted on the balloon, the proximal and distal ends of the balloon tend to first. This pushes the proximal and distal ends of the stent or stent graft towards each other, thereby causing foreshortening. Accordingly, there is a need for a balloon catheter with an apparatus to reduce or eliminate foreshortening when radially expanding in a stent or stent graft mounted thereon.

BRIEF SUMMARY OF THE INVENTION

Embodiments hereof are directed to a stent-graft delivery system comprising. The delivery system includes a balloon, a stent graft mounted over the balloon, and a sleeve disposed over the balloon. The sleeve includes a weakened area between a first end and a second end of the sleeve such that when the balloon is expanded, the balloon expands from a center portion of the balloon towards the ends of the balloon. The sleeve may be disposed over the stent graft such that the stent graft is disposed between the balloon and the sleeve or the stent graft may be disposed over the sleeve such that the sleeve is disposed between the balloon and the stent graft. The weakened area of the sleeve may be a slit, a thinner wall section, grooves, notches, or other weakening features. The sleeve may be adhesively attached to an outer shaft of the catheter or to an outer surface of the balloon.

Embodiments hereof are also directed to a method of deploying a stent graft at a location within a body lumen. The method includes delivering the stent graft to the location. The stent graft is delivered in a radially compressed configuration over a balloon of a stent graft delivery system. The stent graft delivery system also includes a sleeve with a weakened area disposed around the balloon. When at the delivery location, the balloon is inflated such that the stent graft expands from the radially compressed configuration to a radially expanded configuration. The sleeve causes the balloon to expand from a middle portion of the balloon towards ends of the balloon such that the stent graft expands from a middle portion of the stent graft towards ends of the stent graft. After the stent graft is expanded to its radially expanded configuration, the balloon is deflated and the stent graft remains in the radially expanded configuration. The sleeve may be disposed over the stent graft such that the stent graft is disposed between the balloon and the sleeve or the stent graft may be disposed over the sleeve such that the sleeve is disposed between the balloon and the stent graft. The weakened area of the sleeve may be a slit, a thinner wall section, grooves, notches, or other weakening features. The sleeve may be adhesively attached to an outer shaft of the catheter or to an outer surface of the balloon.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. Regarding "proximal" and "distal" positions referenced herein, a proximal end of a prosthesis, e.g., stent-graft, is the end closest to the heart by way of blood flow path whereas a distal end of the prosthesis is the end furthest away from the heart during deployment. In contrast, a distal end of the stent-graft delivery system or other associated delivery apparatus is usually identified as the end that is farthest from the operator, while a proximal end of the delivery system and devices is the end nearest the operator or handle of the catheter.

The following detailed description is merely exemplary in nature and is not intended to limit the invention or the application and uses of the invention. Although the descriptions of embodiments hereof are in the context of treatment of blood vessels such as the aorta and branch vessels that emanate therefrom, the invention may also be used in any other body passageways where it is deemed useful. Furthermore, there is no intention to be bound by any expressed or implied theory presented in the preceding technical field, background, brief summary or the following detailed description.

Figure 1:
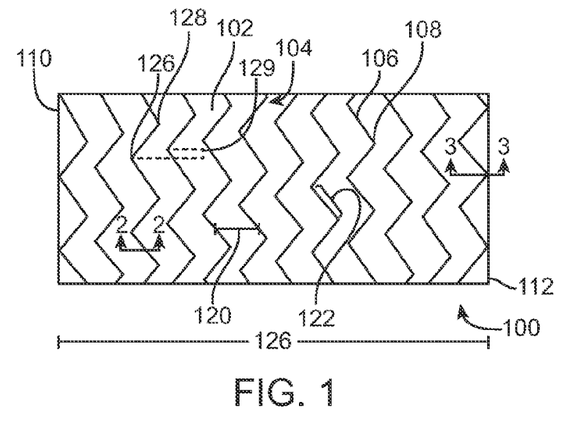
FIG. 1 is a side view of a stent graft in accordance with an embodiment hereof.

FIG. 1 is a side view of a stent graft 100 in accordance with an embodiment hereof. Stent graft 100 includes a graft material 102 and a plurality of stents 104 coupled to graft material 102. Stent graft 100 includes a first end 110 and a second end 112. Stent graft 100 is formed in a tubular shape to form a lumen therethrough, as known in the art.

Figure 2:
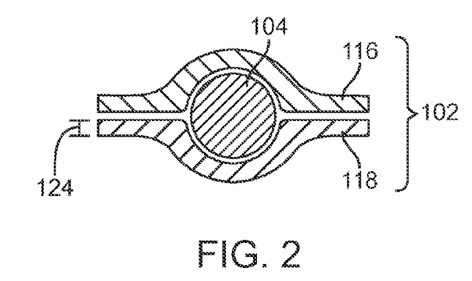
FIG. 2 is a cross-section taken along lines 2-2 of FIG. 1.
Figure 3:
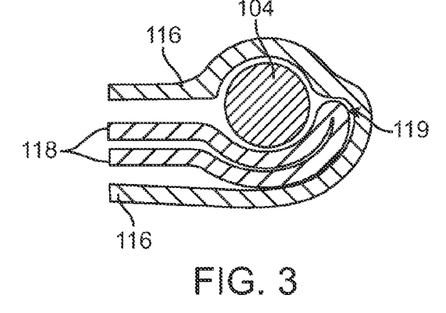
FIG. 3 is a cross-section taken along line 3-3 of FIG. 1.
Figure 3A:
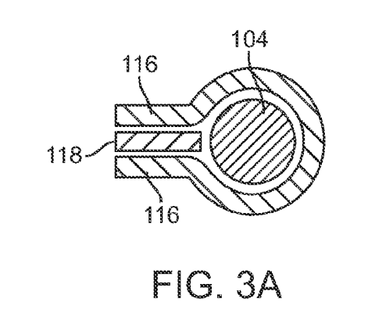
FIG. 3A is another embodiment of the cross-section taken along line 3-3 of FIG.

In order for stent graft 100 to have the desired characteristics of flexibility and durability, graft material 102 is expanded Polytetrafluoroethylene (hereinafter "ePTFE"). Stents 104 are individual rings with a zig-zag or generally sinusoidal shape including a plurality of generally straight segments or struts 106 with adjacent struts connected to each with bends or crowns 108. The stents 104 of stent graft 100 are "segmented" in that the stents are not connected to each other except through the graft material 102. In other words, other than the graft material, other structures, such as longitudinal connectors, do not connect the stents 104 to each other. Such a segmented stent graft 100 improves flexibility of the stent. However, in some instances, it may be acceptable to couple two or three adjacent stents together provided that these coupled stents are segmented from the other stents. For example, and not by way of limitation, in FIG. 1, the left-most two stents 104 could be coupled, then there would be no coupling between the second and third stent. The third and fourth stent could be coupled together with no coupling between the fourth and fifth stent. Further, the coupling could be with a weak or frangible connector such that after deployment, the connector breaks to decouple the stents from each other. Accordingly, stent 104 are not coupled to each other in the radially expanded configuration. Stents 104 are made from a plastically deformable material such that when expanded by a balloon, the stents 104 maintain their radially expanded configuration. Stents 104 may be made from stainless steel, nickel-titanium alloys such as NITINOL, cobalt-chromium alloys, tantalum alloys, various types of polymers or other materials known to those skilled in the art, including said materials coated with various surface deposits to improve clinical functionality. Stents 104 are coupled to graft material 102 by being sandwiched between layers of graft material 102, as shown in FIG. 2. In particular, graft material comprises a first layer 116 and a second layer 118. Although shown as individual layers in FIG. 2, first layer 116 and second layer 118 of graft material 102 are fused together. Further, although two layers 116, 118 are shown, those skilled in the art would understand that each layer 116, 118 maybe formed of several layers of ePTFE. FIG. 3 shows a cross-section of a portion of one of the stents 104 at second end 112 of stent graft 100. As shown in FIG. 3, first and second layers 116, 118 of graft material 102 are folded back under second layer 118 at fold 119. This helps prevent stents 104 at either end of stent graft 100 from protruding through graft material 102 at ends 110, 112 of stent graft 100. However, those skilled in the art would understand that other ways of terminating graft material at ends 110, 112 may also be used. For example, and not by way of limitation, FIG. 3A shows second layer 118 terminating at stent 104, and first layer 116 wrapping around stent 104 and back under second layer 118. Those skilled in the art will recognize that although FIGS. 2-3A show layers 116, 118 as distinct layers with gaps therebetween, when the layers 116, 118 are fused together there will be few, if any, gaps between the layers 116, 118.

In a particular embodiment of a stent graft approximately 3.5 millimeters in diameter, layers 116, 118 of graft material 102 each have a thickness 124 of approximately 0.004 inch and have a density of approximately 0.65 grams/cubic centimeter. Further, a distance 120 between stents 104 is approximately 1 millimeter. Further, a length 122 of struts 106 is approximately 4.5 millimeters and the struts 106 and crowns 108 have a thickness of approximately 0.22 inch. Those skilled in the art will recognize that the specifications for materials and spacing as discussed above are exemplary and other dimensions, thicknesses, sizes, spacing, etc. may be used.

Further, in addition to the parameters discussed above, stents 104 of stent graft 100 may be arranged in a certain manner to improve performance of stent graft 100. For purposes of this discussion bends 108 that open to the right (or point to the left) of stent graft 100 are considered valleys 126 and bends that open to the left (or point to the right) of stent graft 100 are considered peaks 128. The particular arrangement of stent graft 100 includes has valleys 126 of adjacent stents 104 generally aligned but slightly offset from each other, as shown by offset distance 129. As recognized by this range, the valleys 126 may be aligned such that the offset distance is 0 mm. However, the offset distance should not be such that the valley 126 of one of the stents 106 aligned with the peak 128 of an adjacent stent 104.

As noted above, stent graft 100 is "segmented" in that the stents 104 are not connected to each other. Such a segmented stent graft is highly flexible. However, as also noted above, variations in the arrangements of the stents of a stent graft may allow for high flexibility, particularly in regions where such flexibility is necessary, without sacrificing other characteristics of the stent graft. In an embodiment shown schematically in FIG. 4, stent graft 200 FIG. includes a graft material 202 and a plurality of stents 204 coupled to graft material 202. Stent graft 200 includes a first end 210 and a second end 212. Stent graft 100 is formed in a tubular shape to form a lumen therethrough, as known in the art.

Figure 4:
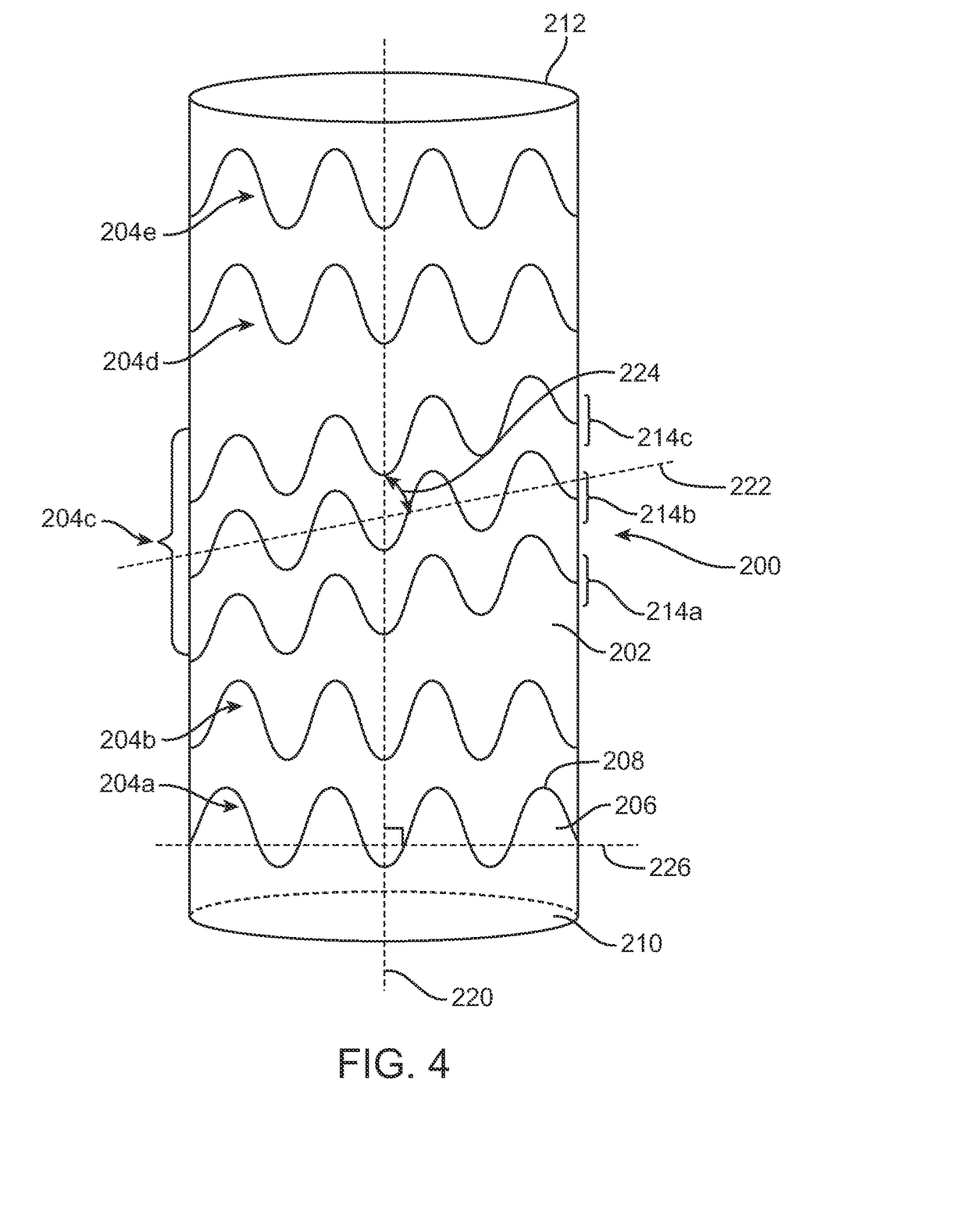
FIG. 4 is schematic view of a stent graft in accordance with an embodiment hereof.

Graft material 202 of stent graft 200 is expanded Polytetrafluoroethylene (hereinafter "ePTFE"). Stent graft 200 is a segmented stent graft as described above. However, the particular arrangement of stents 204 in the embodiment of FIG. 4 differs from FIG. 1. In particular, stents 204a and 204b closest to first end 210 of stent graft 200 are individual rings with a zig-zag or generally sinusoidal shape including a plurality of generally straight segments or struts 206 with adjacent struts connected to each with bends or crowns 208. Stents 204a and 204b are not connected to each other or other stents in FIG. 4 except through the graft material 202. In other words, other than the graft material, other structures, such as longitudinal connectors, do not connect the stents 204a and 204b to each other or to other stents of stent graft 200. Stent graft 200 also includes stents 204d and 204e closest to second end 212 of stent graft 200. Stent 204d and 204e are individual rings with a zig-zag or generally sinusoidal shape including a plurality of struts 206 with adjacent struts connected to each with crowns 208. Stents 204d and 204e are not connected to each other or other stents in FIG. 4 except through the graft material 202. Further, in the middle portion of stent graft 200 between stents 204b and 204d is a helical stent 204c. Helical stent 204c is waveform including struts and crowns, and the waveform is helically wrapped around a circumference to form helically wrapped stent 204c. Helical stent 204c includes a plurality of turns 214, which is defined as the waveform completing a circumference around stent graft 200. In the embodiment shown, helical stent 204c includes three turns 214a-214c. However, those skilled in the art will recognize that fewer or more turns may be utilized. In a helical stent 204c, adjacent turns 214 are connected to each other because the turns are formed by a continuous wire. The waveform is wrapped around the circumference of stent graft 200 at a pitch angle 224 relative to the longitudinal axis 220 of the stent graft 200. Pitch angle 224 is less than 90° relative to longitudinal axis 220. Pitch angle 224 can generally be defined by a line 222 extending through the struts 206 of the waveform, as shown in FIG. 4. However, those skilled in the art recognize that the pitch angle is the angle at which the waveform is wrapped around the circumference. Thus, a line through unusually shaped waveforms may not exactly match the pitch angle. Stents 204a, 204b. 204d, and 204e, as individual stents are not pitched relative to the longitudinal axis 220. Accordingly, a line 226 extending through struts 206 of the individual stents is substantially perpendicular to the longitudinal axis of the stent, as shown in FIG. 4. Stent graft 200 of FIG. 4 is more flexible at each end thereof. Stent graft 200 may be modified to include individual stents only at one end thereof. In particular, in applications where stent graft 200 is a branch stent graft interacting with a fenestration in a main stent graft, the end of the stent interacting with the fenestration may experience larger forces. Non-segmented stent grafts may break in this area. Accordingly, having segmented stents at least at one end of the stent graft prevents such breakage while providing sufficient radial support for the stent graft. The manner in which stents 204 of stent graft 200 are coupled to graft material 202, the materials of stents 204, and other details of stents 204 and stent graft material 202 may be as set forth in other embodiments described herein, or as known to those skilled in the art.

Figure 5:
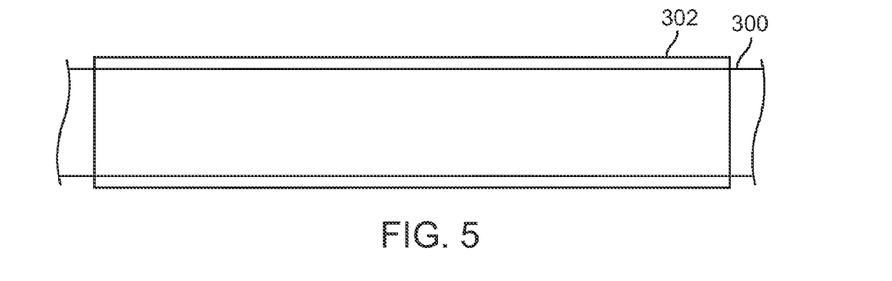
FIGS. 5-9 are schematic views of a method of making a segmented stent graft in accordance with an embodiment hereof.

FIGS. 5-9 show schematically steps in an embodiment of method of making a stent graft. The method may be used to make the stent grafts described herein. However, the stent grafts of FIGS. 1-4 do not need to be made by the method described with respect to FIGS. 5-9. FIG. 5 shows a first step in the method wherein a first layer of ePTFE tubing 302 is positioned over a mandrel 300. The length of ePTFE tubing 302 is greater than the desired length of the stent-graft prosthesis, because ePTFE tubing includes first and second ends which are folded over or cuffed during the manufacturing process. Thus, the length of ePTFE tubing is equal to the desired length of the stent-graft prosthesis plus the length of first and second ends. In order to place the first layer of ePTFE tubing 302 onto mandrel 300, as well as additional layers of material slid over mandrel 300, mandrel 300 may include a tapered expansion tip (not shown) to ease or assist in positioning of tubing over the mandrel. The first layer of ePTFE tubing 300 is slid over the mandrel until it is approximately centered thereon, as shown in FIG. 5.

Figure 6:
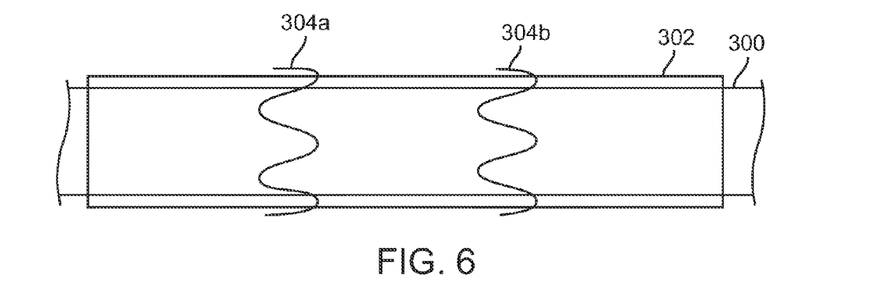

Once first layer of ePTFE tubing 302 in in place, one or more stents 304 are positioned over the first layer of ePTFE tubing 302, as shown in FIG. 6. In the embodiment shown, two stents 304a, 304b are shown and are spaced apart from each other. More or less stents may be placed over first layer 302. Further, a helical stent such as stent 204c of FIG. 4 may be utilized in this step.

Figure 7:
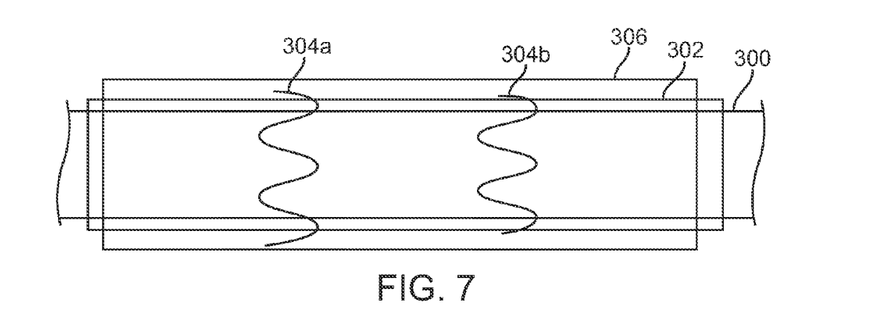

Once stents 304a, 304b are in place, a second layer of ePTFE tubing 306 is positioned directly over the first layer of ePTFE tubing 302 and stents 304a, 304b as shown in FIG. 7. The length of second layer of ePTFE tubing 306 may be approximately equal to the desired length of the stent-graft prosthesis. The second layer of ePTFE tubing 306 is slid over the first layer of ePTFE tubing 302 (and stents 304) until it is approximately centered thereon, as shown in FIG. 7.

Figure 8:
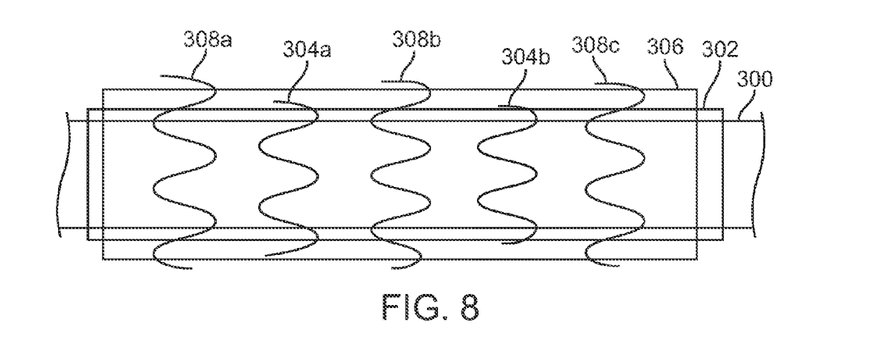

Once second layer of ePTFE tubing 306 in in place, one or more stents 308 are positioned over the second layer of ePTFE tubing 306, as shown in FIG. 8. In the embodiment shown, three stents 308a, 308b, 308c are shown and are spaced apart from each other. Further, stents 304a, 304b are disposed between stents 308a, 308b, 308c such that the stents 304 between first and second layers 302, 306 are staggered with respect to stents 308 over second layer 306. Other arrangements may be utilized. For example, and not by way of limitation, for stent graft 200 shown in FIG. 4, helical stent 204c may be disposed between first and second layers of ePTFE and end stents 204a, 204b, 204d, 204e may be disposed over the second layer of ePTFE, or vice versa. Further, more or less stents may be placed over second layer 306.

Figure 9:
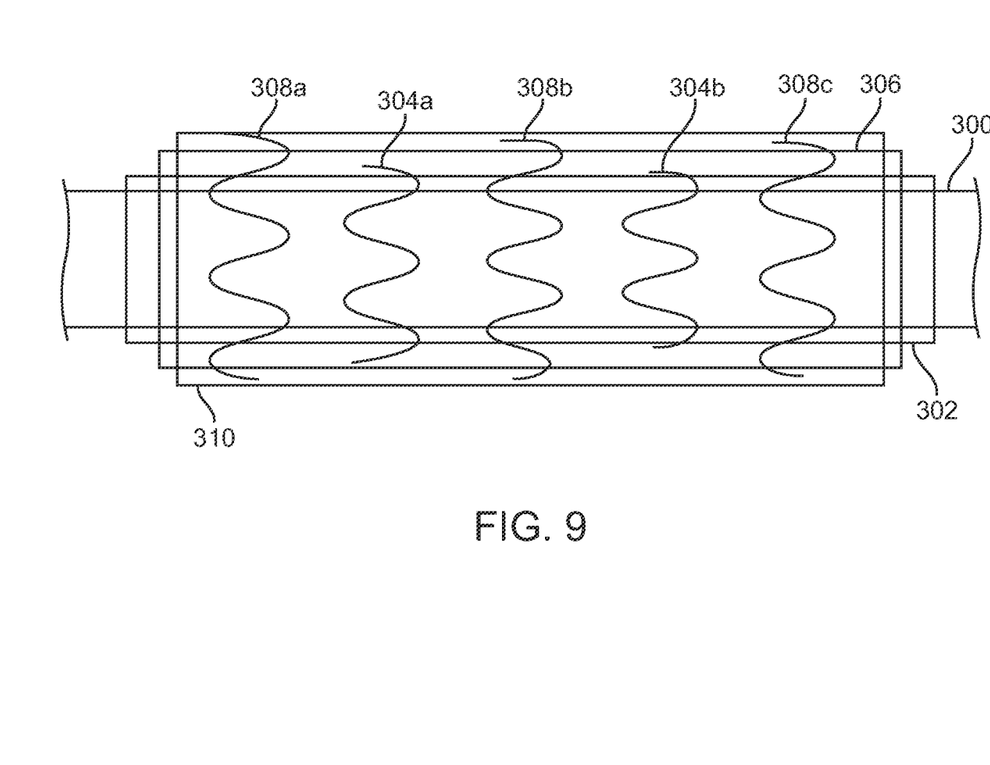

Once stents 308a, 308b, 308c are in place, a third layer of ePTFE tubing 310 is positioned over the second layer of ePTFE tubing 306 and stents 308a, 308b, 308c as shown in FIG. 9. The length of third layer of ePTFE tubing 310 may be approximately equal to the desired length of the stent-graft prosthesis. The third layer of ePTFE tubing 310 is slid over the second layer of ePTFE tubing 306 (and stents 308) until it is approximately centered thereon, as shown in FIG. 9.

Once third layer of ePTFE tubing 310 is in place, ends of first layer 302 may be folded over third layer 310. Then heat shrink tubing (not shown) is slid over the third layer of ePTFE tubing 310 until it is approximately centered thereon. As will be understood by one of ordinary skill in the art, heat shrink tubing is expanded tubing that will shrink when heat is applied thereto in an effort to return or recover to the relaxed diameter it originally had when extruded. When heat shrink tubing shrinks or recovers, it radially compresses the assembled components or layers during a heating step to form the stent-graft prosthesis. The length of the heat shrink tubing is greater than the length of third layer of ePTFE tubing 310 such that the heat shrink material completely/fully covers or extends over the assembled components or layers on mandrel 300.

The assembled layers of ePTFE, stents, and heat shrink tubing are then heated to a desired temperature. This heating step may be accomplished at conditions known to those skilled in the art. For example, and not by way of limitation, conditions, processes, material, and devices described in U.S. patent application Ser. No. 13/674,404, filed Nov. 12, 2012 may be used to heat the mandrel such that the nodes and fibrils of the ePTFE material entangle, intertwine, interweave, or otherwise mesh together, thereby coupling the first, second, and third ePTFE layers together, with the stents captured therebetween. Other methods of heating, such as an air oven and other methods known to those skilled in the art, may also be utilized. Further, other layers such as intermediary layers to assist in process or to prevent sticking such as to the mandrel may also be utilized.

Many balloon expandable stent or stent grafts that are flexible may exhibit undesirable foreshortening or "train-wrecking". FIGS. 10-18 are directed to a balloon catheter 400 including a sleeve 430 configured to reduce or prevent foreshortening. In particular, as shown generally in FIG. 11, balloon catheter 400 includes a proximal portion 402 and a distal portion 404. Balloon catheter 400 as shown includes an outer shaft 408 and an inner shaft 410 disposed in a lumen of outer shaft 408. A lumen 412 of inner shaft 410 is generally known as a guidewire lumen. An annular or inflation lumen 414 is defined between an outer surface of inner shaft 410 and an inner surface of outer shaft 408. Although a dual shaft or "over-the-wire" balloon catheter is shown, other types of balloon catheters known in the art may be used including, but not limited to, rapid exchange catheters. Proximal portion includes a handle or luer 403, such as a Touhy-Borst adapter. Luer 403 includes an opening 405 for a lumen 407 that is coupled to guidewire lumen 412 of an inner shaft 410. Luer 403 also includes an opening 406 for a lumen 409 that is coupled to inflation lumen 414. Proximal portion 402 may include other devices known to those skilled in the art, such as, but not limited to, strain relief elements.

Figure 10:
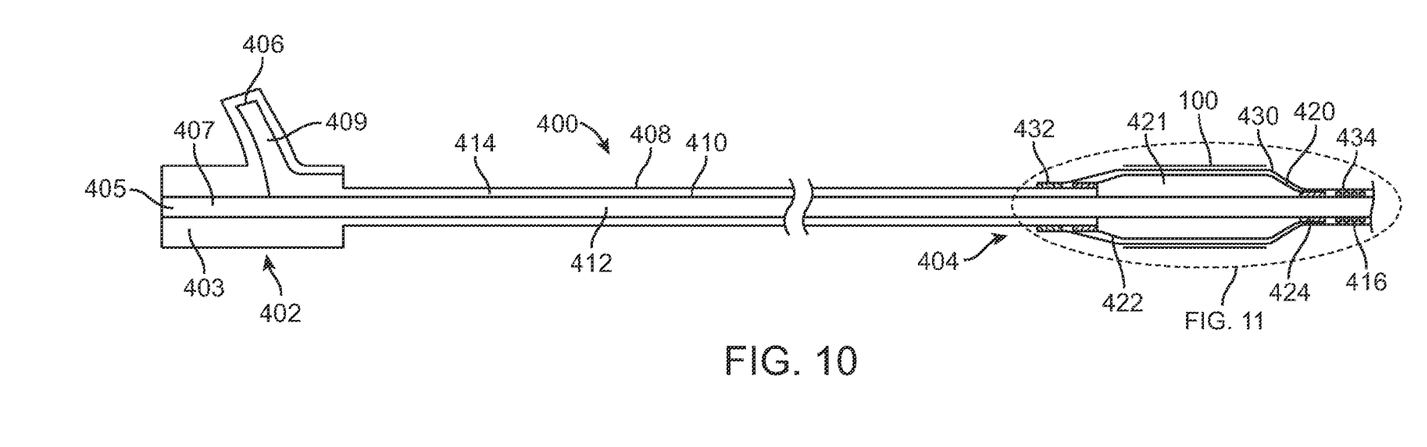
FIG. 10 is a schematic illustration of a balloon catheter with a stent graft mounted thereon in accordance with an embodiment hereof.
Figure 11:
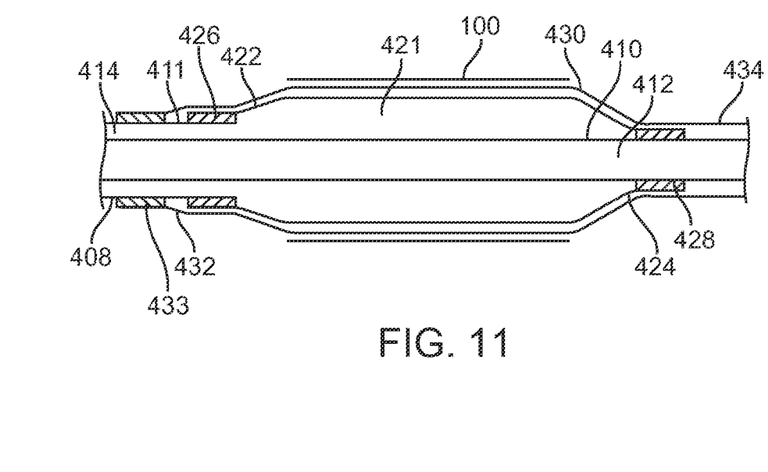
FIG. 11 is a schematic view of a distal portion of the balloon catheter of FIG. 10.

Distal portion 404 of balloon catheter 400 is shown in FIG. 10 and in more detail in FIG. 11. A balloon 420 is disposed at distal portion 404 of catheter 400. In the embodiment shown, a proximal portion 422 of balloon is coupled to an outer surface of a distal portion 411 of outer shaft 410 at connection 426 and a distal portion 424 of balloon 420 is coupled to an outer surface of inner shaft 408 at connection 428. Connections 426 and 428 may be an adhesive or other connections know to those skilled in the art. As shown, inner shaft 408 extends distally beyond a distal end of outer shaft 410. Accordingly, inflation lumen 414 extends into an interior 421 of balloon 420, as known in the art. Although a particular embodiment of a balloon catheter is shown, those skilled in the art would recognize that many variations of a balloon catheter may be utilized.

Figure 12:
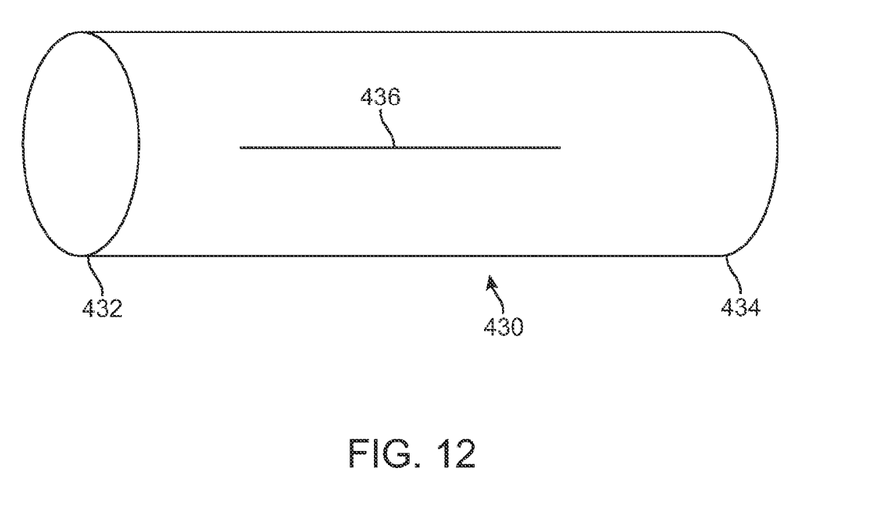
FIG. 12 is a schematic illustration of a sleeve of the catheter of FIG. 10.
Figure 18:
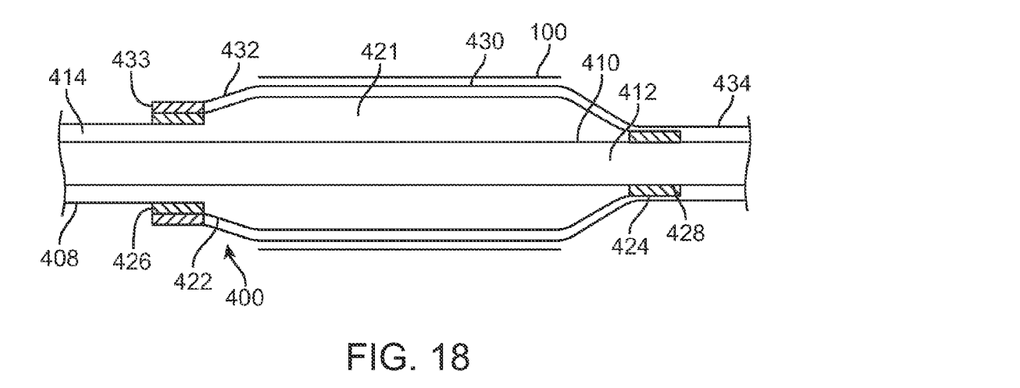
FIG. 18 is a schematic illustration of a distal portion of a balloon catheter with a stent graft mounted thereon in accordance with an embodiment hereof.

Mounted around balloon 420 is a sleeve 430. Sleeve 430 includes a proximal portion 432 and a distal portion 434. Proximal portion 432 of sleeve 430 is mounted to an outer surface of outer shaft 408, as shown at connection 433. Although proximal portion 432 is shown connected to outer shaft 408, proximal portion 432 of sleeve 430 may instead be mounted to an outer surface of proximal portion 422 of balloon 420, as shown in FIG. 18. Connection 433 may be an adhesive connection, a fusion connection, or a mechanical connection such as a bracket or clamp. As shown in FIG. 12, sleeve 430 is a thin-walled flexible sleeve with a weakened area 436 disposed generally in the center of the sleeve 430 between proximal portion 432 and distal portion 434 of sleeve 430. Weakened area 436 may be a slit, grooves, notches, or other modifications to sleeve 430 to make the weakened area 436 resist expansion of balloon 420 less than the remaining areas of sleeve 430. For example, and not by way of limitation, another way to form weakened area 436 may be to make the center portion of sleeve 436 thinner than the remainder of sleeve 430. Although weakened area 436 is shown on one side of sleeve 430, weakened areas could be disposed at several locations around the circumference of sleeve 430 in the center portion of sleeve 430 or continuously around the circumference of sleeve 430 in the center portion of sleeve 430. Accordingly, as explained in more detail below, when balloon 420 is expanded, weakened area 436 of sleeve 430 offers less resistance to the expansion of balloon 420 than the remaining area of sleeve 430. Therefore, balloon 420 expands from the center of balloon 420 towards the proximal and distal ends 422, 424. Sleeve 430 may be formed of any thin-walled flexible material. For example, and not by way of limitation, sleeve 430 may be formed from a polyamide such as nylon, a fluoropolymer such as Polytetrafluoroethylene (PTFE), a thermoplastic elastomer such as polyether block amide (PEBA), thermoplastic polyurethane or other materials known to those skilled in the art.

A stent graft 100 is mounted around sleeve 430 and balloon 420 in a radially compressed configuration, as shown in FIGS. 10 and 11. Although stent graft 100 is referred to, it need not be the stent graft 100 of FIGS. 1-3. Any balloon expandable stent graft may be used. Further, instead of a stent graft, a stent may be mounted around balloon 420.

Figure 13:
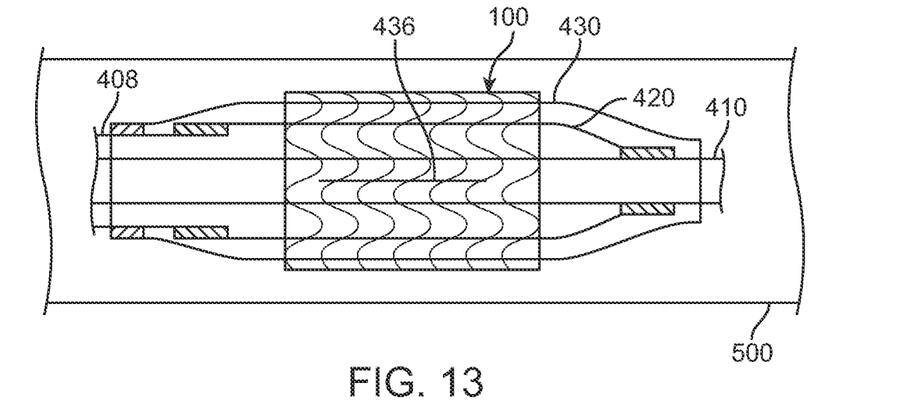
FIGS. 13-17 are schematic illustrations depicting a method of deploying a balloon expandable stent graft using the balloon catheter of FIG. 10.

FIGS. 13-17 show a method of deploying stent graft 100 in a vessel 500 to reduce foreshortening. As shown in FIG. 13, catheter 400 is delivered within a vessel 500 to a deployment site. Catheter 500 can be inserted into vessel 500 and delivered through the lumen of vessel 500 by methods known to those skilled in the art. For example, and not by way of limitation, and access opening may be formed into the femoral artery by the Seldinger technique. A guidewire (not shown) may be inserted into vessel 300 and advanced to the deployment site. Catheter 500 may then be advanced along the guidewire to the deployment site, as known in the art.

Figure 14:
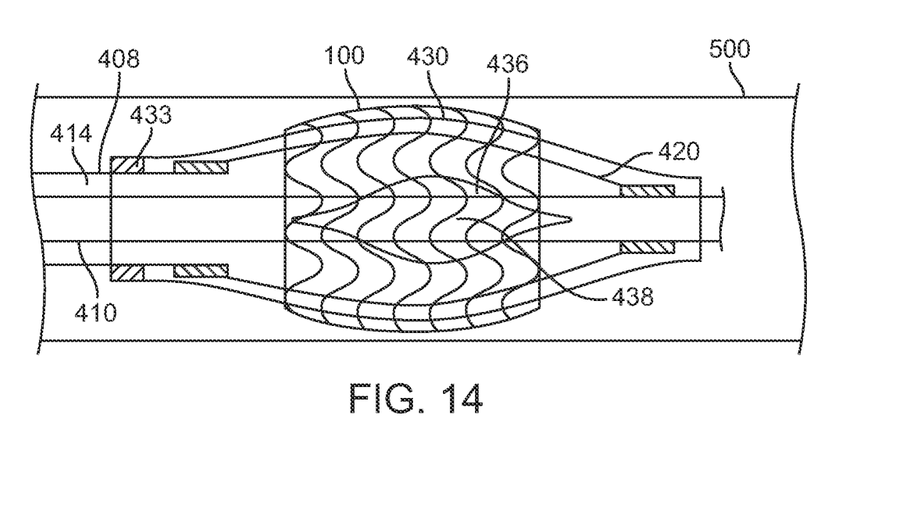

Upon reaching the deployment site, a fluid is inserted through opening 406 in luer 403 and into inflation lumen 414. The fluid may be any fluid suitable for use in inflatable a balloon, such as, but not limited to, a saline solution. The inflation fluid travels from inflation lumen 414 into interior 421 of balloon 420. As interior 421 fills, balloon 420 expands, as shown in FIG. 14. Because weakened areas 436 of sleeve 430 provides less resistance to the expansion of balloon 420, balloon 420 begins expansion at weakened area 436. As balloon 420 expands from its center outward towards proximal and distal portions 422, 424, stent graft 100 mounted on sleeve 430 also expands from its center towards its first and second ends 110, 112. Further, in the embodiment shown in FIGS. 13-17, weakened area 436 is a slit. Therefore, as balloon 420 expands and expands sleeve 430, the slit of weakened area 436 begins to propagate, thereby tearing sleeve 430, as shown in FIG. 14.

Figure 15:
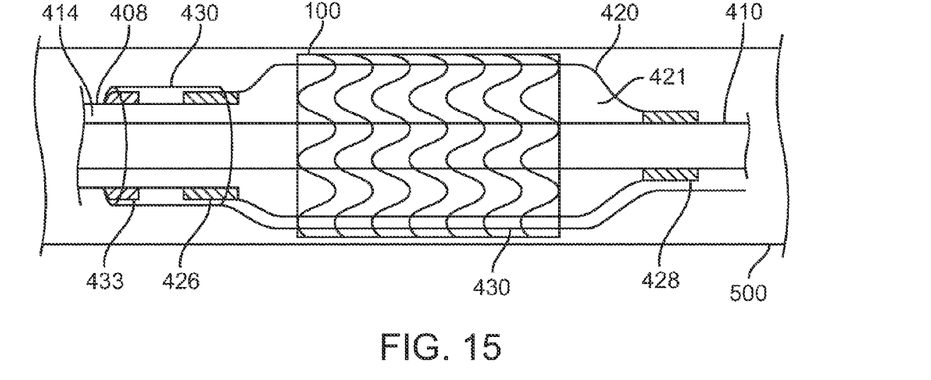
Figure 16:
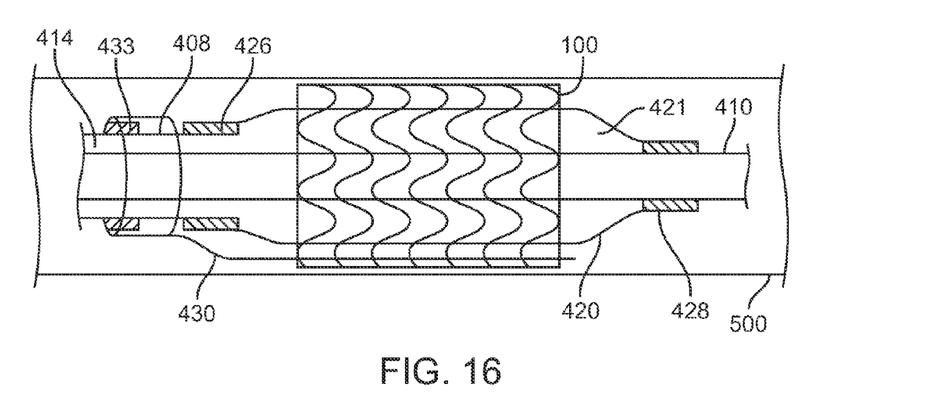
Figure 17:
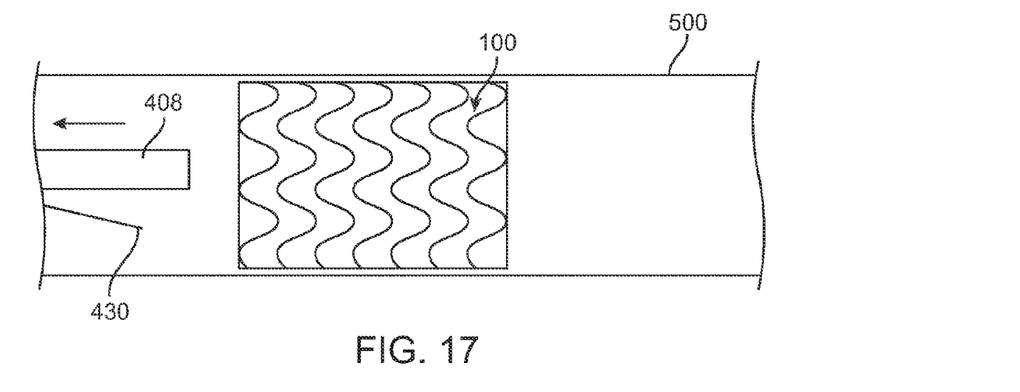

As the expansion fluid continues to fill interior 421 of balloon 420, balloon 420 fully expands, as shown in FIG. 15. Such full expansion of balloon 420 also fully expands stent graft 100, thereby deploying stent graft 100. Further, the slit of weakened area 436 propagates such that sleeve 430 is fully torn. However, those skilled in the art would recognize that sleeve 430 need not be fully torn. After stent graft 100 has been expanded, the inflation fluid is drained from inflation lumen 414 and the interior 421 of balloon 420, thereby deflating balloon 420, as shown in FIG. 16. Then, as shown in FIG. 17, catheter 400 may be withdrawn proximally in the direction of the arrow shown in FIG. 17. This withdrawal of catheter 700 also pulls any portion of sleeve 430 disposed between stent graft 100 and balloon 420.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent graft delivery system comprising:
    a balloon;
    a sleeve disposed over the balloon, wherein the sleeve includes a weakened area between a first end and a second end of the sleeve; and
    a stent graft mounted over the sleeve, the stent graft including a stent coupled to a graft material,
    wherein the balloon and sleeve are configured such that upon inflation, the balloon expands from a middle portion of the balloon towards ends of the balloon such that the stent graft expands from a middle portion of the stent graft towards ends of the stent graft.

2. The delivery system of claim 1, wherein the weakened area comprises a portion of the sleeve with a thinner wall than the remainder of the sleeve.

3. The delivery system of claim 1, wherein the weakened area comprises a slit in the sleeve.

4. The delivery system of claim 3, wherein the slit extends from an outer surface of the sleeve to an inner surface of the sleeve.

5. The delivery system of claim 1, wherein the first end of the sleeve is proximal to the second end and wherein the first end of the sleeve is adhesively coupled to the balloon.

6. The delivery system of claim 1, wherein the balloon is coupled to a shaft of a catheter.

7. The delivery system of claim 6, wherein a proximal end of the balloon is coupled to an outer shaft of the catheter and a distal end of the balloon is coupled to an inner shaft of the catheter.

8. The delivery system of claim 7, wherein a proximal end of the sleeve is coupled to a distal portion of the outer shaft.

9. The delivery system of claim 7, wherein a proximal end of the sleeve is coupled to a proximal portion of the balloon.

10. A method of delivering and deploying a stent graft to a location within a body lumen comprising the steps of:
    delivering the stent graft to the location, wherein the stent graft is in a radially compressed configuration mounted over a balloon of a stent graft delivery system, wherein a sleeve with a weakened area is disposed around the balloon;
    inflating the balloon such that the stent-graft expands from the radially compressed configuration to a radially expanded configuration, wherein the sleeve causes the balloon to expand from a middle portion of the balloon towards ends of the balloon such that the stent graft expands from a middle portion of the stent graft towards ends of the stent graft; and
    deflating the balloon, wherein the stent-graft remains in the radially expanded configuration after deflating of the balloon.

11. The method of claim 10, wherein the weakened area comprises a slit through the sleeve.

12. The method of claim 11, wherein the slit extends from an outer surface of the sleeve to an inner surface of the sleeve.

13. The method of claim 10, wherein the weakened area comprises a portion of the sleeve with a thinner wall than the remainder of the sleeve.

14. The method of claim 10, wherein the stent graft is disposed over the sleeve such that the sleeve is disposed between the balloon and the stent graft.

\* \* \* \* \*